United States Patent
Pisharodi

[11] Patent Number: 5,693,100
[45] Date of Patent: *Dec. 2, 1997

[54] MIDDLE EXPANDABLE INTERVERTEBRAL DISK IMPLANT

[76] Inventor: Madhavan Pisharodi, 844 Central Blvd., Suite 1200, Brownsville, Tex. 78520

[*] Notice: The term of this patent shall not extend beyond the expiration date of Pat. No. 5,171,278.

[21] Appl. No.: 617,490

[22] Filed: Mar. 15, 1996

Related U.S. Application Data

[63] Continuation of Ser. No. 479,547, Jun. 7, 1995, abandoned, which is a continuation of Ser. No. 316,806, Oct. 3, 1994, abandoned, which is a continuation of Ser. No. 106,148, Aug. 13, 1993, abandoned, which is a continuation of Ser. No. 786,758, Nov. 1, 1991, abandoned, which is a continuation-in-part of Ser. No. 659,758, Feb. 22, 1991, Pat. No. 5,171,278.

[51] Int. Cl.⁶ .................................................. A61F 2/44
[52] U.S. Cl. .................................................. 623/17
[58] Field of Search ................. 623/17; 606/60, 606/61, 63; 269/48.1, 48.3

[56] References Cited

U.S. PATENT DOCUMENTS

| | | | |
|---|---|---|---|
| 725,874 | 4/1903 | Riley | 269/48.1 |
| 2,226,078 | 12/1940 | Spahn | 269/48.1 |
| 3,030,903 | 4/1962 | Morris | 269/48.1 |
| 3,648,294 | 3/1972 | Shahrestani . | |
| 3,867,728 | 2/1975 | Stubstad et al. . | |
| 3,986,383 | 10/1976 | Petteys | 269/48.1 X |
| 4,309,777 | 1/1982 | Patil . | |
| 4,401,112 | 8/1983 | Rezaian | 606/61 |
| 4,465,220 | 8/1984 | Ledlow et al. | 269/48.1 X |
| 4,553,273 | 11/1985 | Wu | 623/18 |
| 4,657,550 | 4/1987 | Daher | 606/61 X |
| 4,759,769 | 7/1988 | Hedman et al. | 623/17 |
| 4,772,287 | 9/1988 | Ray et al. | 128/69 X |
| 4,834,757 | 5/1989 | Brantigan | 623/17 |
| 4,863,476 | 9/1989 | Shepperd | 623/17 |
| 4,863,477 | 9/1989 | Monson | 623/17 |
| 4,932,969 | 6/1990 | Frey et al. | 623/17 |
| 4,932,975 | 6/1990 | Main et al. | 606/61 X |
| 5,002,576 | 3/1991 | Fuhrmann | 623/17 |
| 5,059,193 | 10/1991 | Kuslich | 606/61 |
| 5,171,278 | 12/1992 | Pisharodi | 623/17 |
| 5,290,312 | 3/1994 | Kojimoto et al. | 623/17 |
| 5,390,683 | 2/1995 | Pisharodi | 128/898 |
| 5,522,899 | 6/1996 | Michelson | 623/17 |

FOREIGN PATENT DOCUMENTS

| | | | |
|---|---|---|---|
| 0260044 | 3/1988 | European Pat. Off. . | |
| 0304305 | 2/1989 | European Pat. Off. . | |
| 2639823 | 6/1990 | France | 623/17 |
| 0038822 | 8/1965 | Germany | 269/48.1 |
| 2701279 | 7/1977 | Germany | 606/63 |
| 3729600 | 3/1989 | Germany | 623/17 |
| 662082 | 12/1977 | U.S.S.R. . | |
| 0662082 | 5/1979 | U.S.S.R. | 606/63 |
| 1127905 | 5/1979 | U.S.S.R. . | |
| 0906548 | 2/1982 | U.S.S.R. | 606/63 |
| 906548 | 2/1982 | U.S.S.R. . | |
| 1122304 | 11/1984 | U.S.S.R. | 606/63 |

*Primary Examiner*—David H. Willse
*Attorney, Agent, or Firm*—Mark R. Wisner

[57] ABSTRACT

Artificial disk implant and methods for implanting same, the implant, in one embodiment, having a member for adapting in size and shape to the anatomical space between vertebrae, and apparatus for expanding the member to conform to the space. In one preferred embodiment, there is provided an artificial intervertebral disk implant having a cylindrical body comprised of cylindrical subunits capable of expansion. In another preferred embodiment, rectangular subunits capable of expansion are provided. The implant can be used alone or in various combinations for the purpose of spinal fusion.

9 Claims, 2 Drawing Sheets

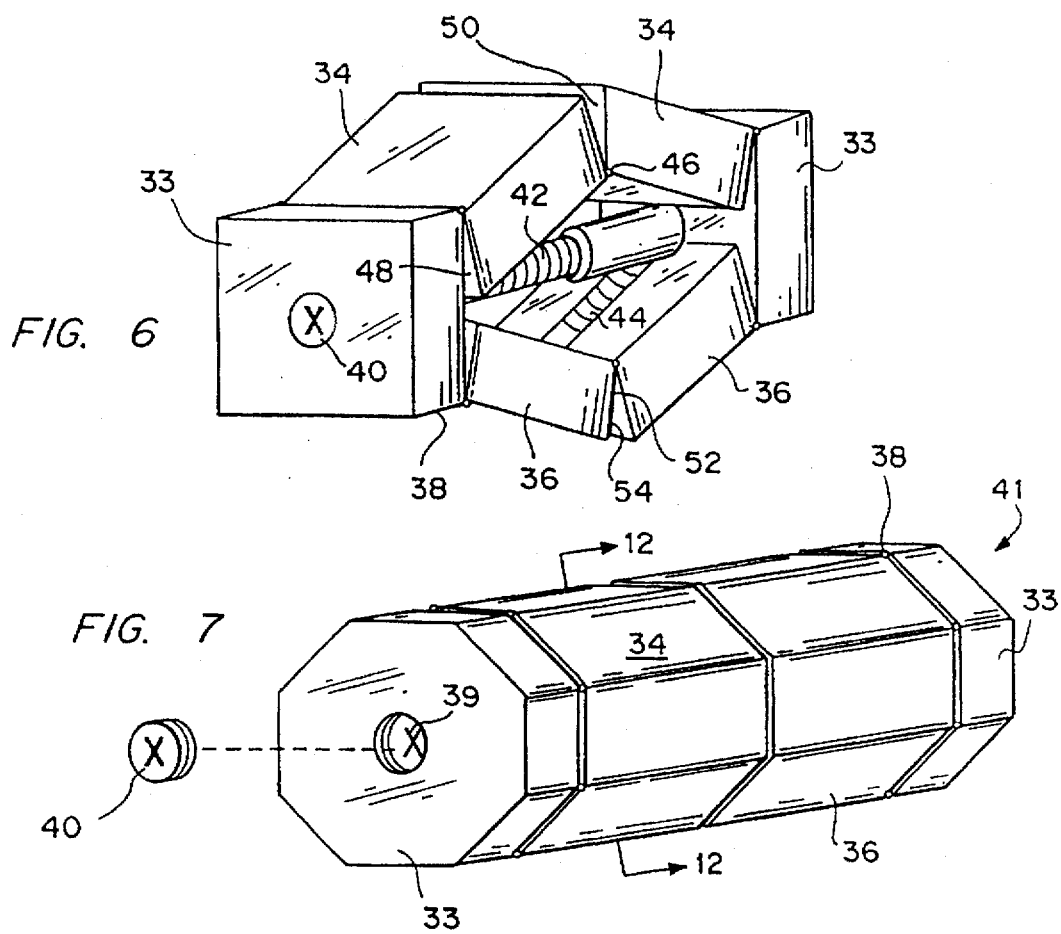
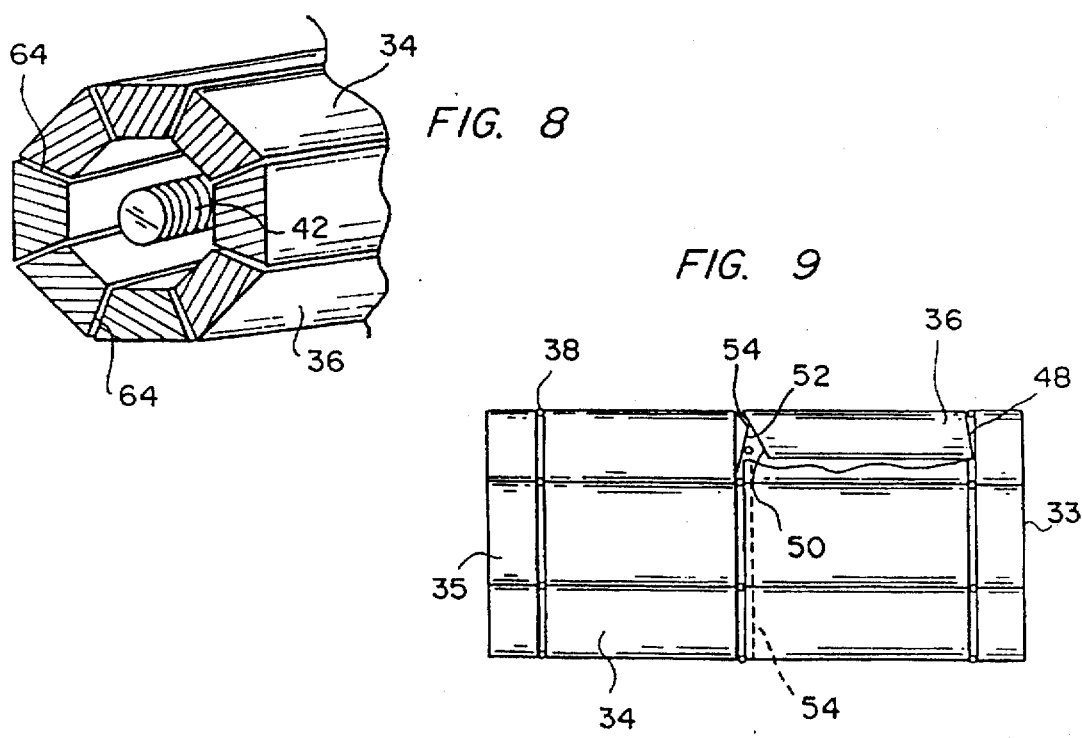

MIDDLE EXPANDABLE INTERVERTEBRAL DISK IMPLANT

RELATED APPLICATIONS

This application is a continuation of application Ser. No. 08/479,547, filed on Jun. 7, 1995, now abandoned, which is a continuation of application Ser. No. 08/316,806, filed on Oct. 3, 1994, now abandoned, which is a continuation of application Ser. No. 08/106,148, filed on Aug. 13, 1993, now abandoned, which is a continuation of application Ser. No. 07/786,758, filed on Nov. 1, 1991, now abandoned, which is a continuation-in-part of application Ser. No. 07/659,758, filed on Feb. 22, 1991, now U.S. Pat. No. 5,171,278 issued on Dec. 15, 1992. Also filed on Feb. 22, 1991 was Applicant's application entitled Artificial Spinal Prosthesis, a copy of which was submitted therewith, and which is now issued as U.S. Pat. No. 5,123,926.

BACKGROUND OF THE INVENTION

1. Field of the Invention

This invention relates to an intervertebral disk implant. More specifically, the present invention relates to cylindrical and rectangular disk implants which are expandable in the middle, or central portions, which are used alone or in various combinations for the purpose of spinal fusion.

2. Description of the Related Art

The spine is a flexible structure comprised of thirty-three vertebrae. The vertebrae are separated and cushioned from each other by fibrous cartilage in structures called intervertebral disks. If the spine is injured or becomes diseased, surgical intervention involving removal of one or more of these disks, and fusion of the adjacent vertebrae, may be indicated. Such disk injuries can happen in the neck, in the thoracic region and in the lumbar region. The more frequent injuries are in the lower lumbar and in the lower cervical regions.

Treatment of a herniated disk in the neck and in the lumbar region continues to be a challenging field of medicine. The classical treatment for a ruptured disk continues to be removal of the disk from between the vertebrae. In this process, a defect is made which continues to bother the patients throughout the rest of their lives. One additional procedure previously attempted is to replace the disk space with a bone graft, bringing about fusion of the vertebrae above and below the disk, eliminating the empty space between the vertebrae.

Theoretically a diskectomy with fusion is a satisfactory procedure, though not ideal because the replaced bone does not have any of the functions of the cartilage tissue of the disk, i.e. no cushioning effect. This procedure, however, is technically demanding and has medical complications because of several physiological factors. First of all, the bone plug used to pack the disk space does not conform to the shape of the disk because the disk bulges maximally in the center. The disk space is wider in the middle and narrower at its anterior and posterior ends. It is impossible to insert a bone plug having its maximum width at the center because it cannot be inserted through the mouth of the disk space. For this reason, the various bone plugs which are currently available commercially have only four point contacts, i.e. at the front and back part of the disk space. Secondly, if the bone pieces do not fuse within a minimum period of time, they dissolve, become thinner and may eventually extrude out of the disk space, causing pressure on the nerve roots.

Various prosthetic disk plugs are disclosed in the art, but all are characterized by the limitation of not conforming to the shape of the disk space. For instance, U.S. Pat. No. 4,863,476 describes a spinal implant which is an elongated body divided longitudinally into two portions having a cam device movable there-between for increasing the space between the two body portions, but is generally cylindrical in shape such that the only contact points are at the front and the back of the disk space. The art also discloses intervertebral disk prosthesis (e.g., U.S. Pat. Nos. 3,867,728, 4,309,777, 4,863,477 and 4,932,969 and French Patent Application No. 8816184 (Publication No. 2,639,823) which may have more general contact with the adjacent disks, but which are not intended for use in fusion of the disks. The art also includes spinal joint prostheses such as is described in U.S. Pat. No. 4,759,769, which is again not indicated for use when fusion is the preferred surgical intervention.

From this prior art, it is apparent that there has long been a need for a disk plug, or implant, capable of supporting the disk space after a simple diskectomy for fusion of adjacent vertebrae, and the object of the present invention is to provide such an implant.

SUMMARY OF THE INVENTION

An intervertebral disk implant is described for implantation into the disk space after surgical removal of a diseased or damaged intervertebral disk. Implants according to this invention include means for changing the shape of the implant to adapt to the shape of the anatomical region of the disk space by expanding the implant to conform to a portion of that space.

In one preferred embodiment, there is provided an intervertebral disk implant with a cylindrical body comprised of cylindrical subunits capable of radially outward expansion. In another preferred embodiment, there is provided an intervertebral disk implant having a rectangular body comprised of substantially rectangular subunits capable of radially outward expansion. Both the cylindrical and rectangular implants are disk plugs expandable in the middle portion to provide contact with substantially the entire area of the disk space against the vertebral bodies.

In a preferred method in accordance with the present invention, there is provided a method of fusing two adjacent vertebrae after removal of the disc from there-between which comprises the steps of inserting a disk implant into the disk space, expanding a portion of the implant intermediate the ends thereof outwardly in a radial direction, injecting cancellous bone chips into the disk space medial to the disk plug, and applying a physiologically compatible adhesive over the cancellous bone chips medial to the disk plug to close off the remaining portion of the opening of the disk space.

The present invention recognizes and addresses the previously-mentioned long felt needs and provides satisfactory solution to this need in its various possible embodiments. To one of skill in this art who has the benefits of this invention's teaching and disclosures, other and further objects and advantages will be clear, as well as others inherent therein, from the following description of the presently-preferred embodiments thereof, given for the purpose of disclosure, when studied in conjunction with the accompanying drawings. Although these descriptions are detailed to insure adequacy and aid understanding, this detail is not intended to prejudice that purpose of a patent which is to claim an invention, no matter how others may later disguise it, by variations in form or addition of further improvements.

BRIEF DESCRIPTION OF THE DRAWINGS

So that the manner in which the above cited features, advantages, and objects of the invention, as well as others which will become clear, are attained, more particular description of the invention briefly summarized above may be had by reference to certain embodiments thereof which are illustrated in the appended drawings, which drawings form a part of the specification. It is to be noted, however, that the appended drawings illustrate presently preferred embodiments of the invention and are therefore not to be considered limiting of its scope, for the invention may include equally effective equivalent embodiments.

In the accompanying drawings,

FIG. 6 is a projected view of the disk implant of FIG. 5 after expansion of the intermediate portion thereof.

FIG. 7 is a projected view of an alternative embodiment of the disk implant of FIG. 5.

FIG. 8 is a cross section view of the disk implant of FIG. 7 taken along the line 8—8.

FIG. 9 is a side view of the disk implant of FIG. 7 showing a portion of one of the intermediate members broken away therefrom.

DETAILED DESCRIPTION OF THE INVENTION

Figure 1:
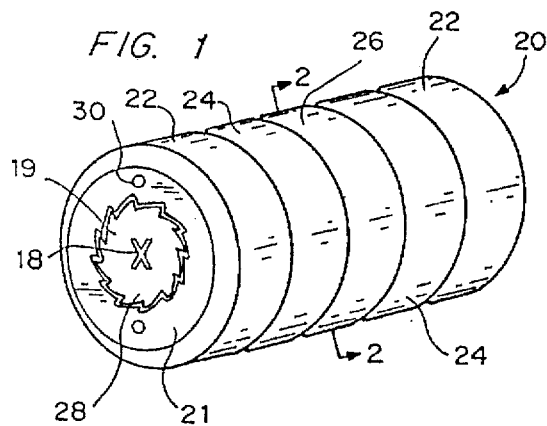
FIG. 1 is a projected view of one presently preferred embodiment of the disk implant of the present invention.

The disk implants of the present invention can be understood with reference to FIGS. 1 to 9 in which the numerals represent like parts. FIG. 1 depicts a cylindrical embodiment of the present invention. A disk implant 20 is comprised of a strong thin non-porous material. Suitable materials for the disk implant 20 include modified carbon, titanium, steel, physiologically inert and/or medically compatible polymers such as a urethane or DELRIN® polymer, or any surgical implant, or any biologically compatible material. The disk implant 20 is comprised of a plurality of subunits 22, 24 and 26, and screw 28 is turned to cause expansion of subunits 24 and 26. The subunits 24 and 26 are preferably comprised of a material which is capable of maintaining spring tension and are mounted to and wound around an elongate central longitudinal axis in the form of central rod 25 (see FIGS. 2 and 3). Because of this structure, each of the subunits is conveniently referred to herein as including a coiled member, or sheet, as identified at reference numeral 32 in FIG. 2.

Each coiled member, or sheet, 32 is mounted to central rod 25 by welding, riveting, or by other manner depending upon the material(s) comprising the sheet 32 and central rod 25 as known in the art. In the preferred embodiment shown in FIGS. 1–4, the central rod 25 is provided with a flat 23 to provide a stable surface for mounting of the sheet 32 thereto with, for instance, a tack weld. At the other, free end of each sheet, or coiled member 32, the coiled member 32 is beveled as at reference numeral 33 so as to provide a smooth, generally round exterior surface on each of the subunits 24 and 26 and to facilitate the sliding of the coiled member 32 past the free end thereof as the subunits 24 and 26 are expanded radially outwardly as described below.

Figure 2:
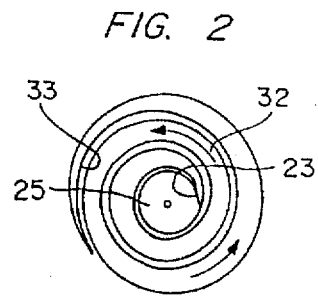
FIG. 2 is a cross section view of the disk implant of FIG. 1 taken along the line 2—2 in FIG. 1.
Figure 3:
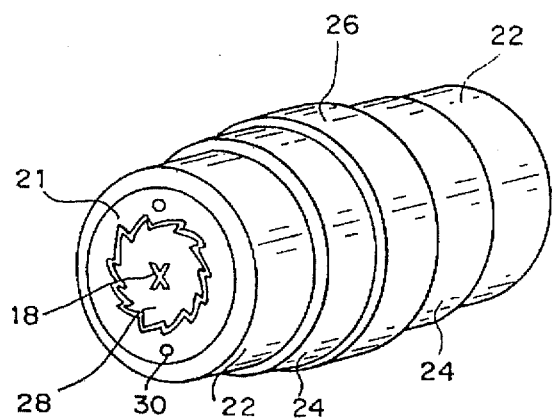
FIG. 3 is a projected view of the central axis of the disk implant of FIG. 1 having the members coiled therearound removed therefrom.

As shown in FIG. 3, central rod 25 is provided with a portion 29 approximately mid-way between the ends thereof having a larger diameter than the rest of the central rod 25 for a purpose to be made clear below. A Phillips head-type slot 18 is provided at one end of the central rod 25 for rotation of the rod 25 as described below, and the end of the rod 25 is provided with a head 28 having a plurality of teeth 19 for interdigitating with the reciprocal cavities in the lock nut 21 to prevent rotation of central rod 25. The Allen screws 30 are loosened to force lock nut 21 away from the end surface 27 of subunit 22 so that the teeth 19 on the head 28 of central rod 25 are disengaged from the cavities in lock nut 21 to allow rotation of rod 25. Alternatively, either rod 25 or lock nut 21 is comprised of a resilient, medically compatible polymer material which allows rotation of the teeth 19 past the cavities in lock nut 21 in one direction but not the other. The expanded shape of the disk implant 20 is shown in FIG. 2. Turning screw or bolt 28 allows for maximal expansion of the subunit 26 and moderate expansion of the subunit 24 because the sheet 32 comprising subunit 26 is mounted to the rod 25 on the portion 29 of larger diameter while each of the sheets 32 comprising subunits 22 and 24 is mounted to central rod 25 in between the portion 29 thereof and the subunits 22.

Turning of central rod 25 using the slot 18 in screwhead 28 expands subunits 24 and 26 which remain in an expanded shape due to the interaction of the teeth 19 and the cavities in lock nut 21 and the compression of the implant 20 between the two vertebrae above and below the implant 20 once inserted into the disk space. In other words, engagement of the adjacent vertebrae prevents the slipping of the free ends of the sheets 32 around the outside circumference of implant 20 such that the sheets 32 do not "re-wind" after being expanded to the position shown in FIG. 4. Removal of lock nut 21 is accomplished by turning of the allen screw 30 which holds lock unit 21 to subunit 22.

Lock nut 21 is inlaid into end subunit 22 and is fixed by the allen screw 30. Lock nut 21 is removed if the implant 20 has to be removed.

FIG. 2 illustrates a cross section of the disk implant 20. By use of the central rod with sections of different diameters (see FIG. 3) and thicknesses of the cylindrically wound sheet 32, the subunits 24 and 26 can be expanded as desired. The cylindrical disk implant 20 is expanded as the sheets 32 are uncoiled. Generally, any method that allows for expansion of the cylindrical embodiment of the disk implant may be used. For the cylindrical disk implant 20, turning the central rod 25 uncoils the sheets 32 because the inside end of the sheet 32 is attached to the central rod 25.

Figure 4:
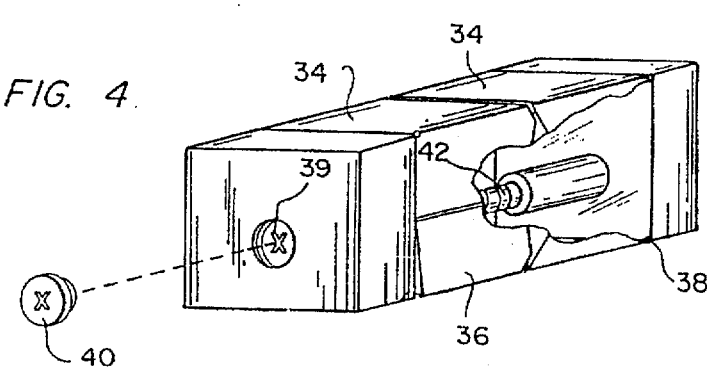
FIG. 4 is a projected view of the implant of FIG. 1 after expansion of the intermediate portion thereof.

FIG. 4 illustrates the cylindrical disk implant 20 in its expanded form. In its expanded form, the implant cannot be removed from the disk space.

Figure 5:
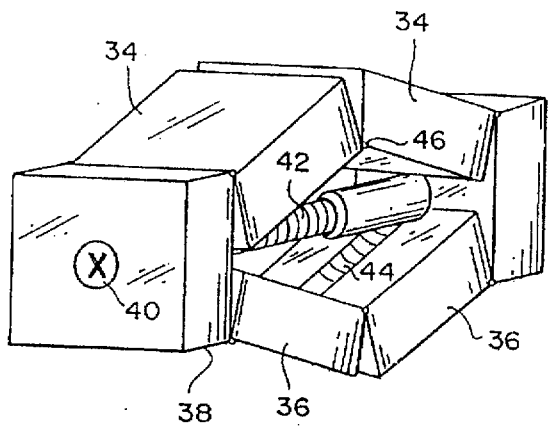
FIG. 5 is a projected view of a second presently preferred embodiment of the disk implant of the present invention.

FIG. 5 depicts a rectangular disk implant 31 according to the present invention. Turning Phillips head 39 of screw 42 encapsulated in a sheath 44 (best shown in FIG. 6) formed in the intermediate subunits 34 and 36 causes the radially outward expansion of superior intermediate subunits 34 superiorly and inferior intermediate subunits 36 inferiorly. Although shown in FIGS. 5 and 6 with two of the hinged members, or subunits 34, it will be understood by those skilled in the art who have the benefit of this disclosure that the plug, or implant, 31 may be provided with four, eight, or even more of the hinged intermediate subunits 34 and 36 as shown at reference numeral 41 in FIG. 7. The expanded shape of the rectangular disk plug 31 is illustrated in FIG. 6. Intermediate parts 34 and 36 are secured to an end cap or subunit 33 by hinge 38. Intermediate parts 34 and 36 are secured to each other by hinge 46. Upon rotation of screw 42 using a conventional screwdriver and the Phillips head slot 39, the end caps 33 are drawn closer together by movement along the threads of screw 42. To insure that the subunits 34 and 36 expand radially outwardly from screw 42, the ends 48 of each respective subunit 34 and 36 abutting the end caps 33 are angled so as to create a force vector outwardly away from screw 42 when end cap 33 exerts pressure on the surface 48, the hinge 38 being mounted in the acute angle formed by surface 48 and end cap 33. In one particularly preferred embodiment (best shown in FIGS. 7–9 and discussed below), the tendency of this force vector to cause the subunits 34 and 36 to expand is increased by angling the face 50 of one subunit 34 or 36 in the same direction as the angle in the surface 48. The surface 52 of the opposed subunit 34/36 is similarly angled, but with a bearing surface 54 formed therein that is angled in the same direction as the angle in surface 48 and face 50 so that the face 50 rides upwardly onto bearing surface 54 to translate the opposed, end-to-end force vectors applied to end caps 33 by rotation of screw 42 into a force vector having a radially outward (from screw 42) component. By referring to FIGS. 7–9, it can be seen that the radially outward expansion caused by rotation of the screw 42 effectively simulates the opening of two opposed umbrellas, and the particular embodiment shown in those figures may be conveniently referred to as having a "double umbrella" configuration.

A threaded lock nut 40 is inserted over Phillips screw head 39 (see FIG. 5). Lock nut 40 prevents the subunits from moving from the expanded shape. Removing lock nut 40 provides access to screw head 39 to allow subunits 34 and 36 to return to the position shown in FIG. 5.

The cylindrical 20 and 41 and rectangular 31 implants are inserted after a simple diskectomy. Ordinarily, the size of the disk implant is approximately 2.5 to 3.5 centimeters in length and 1.0 to 1.5 centimeters in height and width.

FIG. 8 shows a projected view of the disk implant 41 shown in FIG. 7 having the subunits 34 and 36 cut in section. This view shows how the hinged intermediate subunits 34 and 36 fit together in the unexpanded position due to their beveled sides 64.

The hinged subunits 34 and 36 of implants 31 and 41 may also be comprised of a single piece (not shown) of resilient material having a central slot formed therein extending radially outwardly from the screw 42 forming the central axis of the implant. These slots allow the hinged subunits to bend in a radially outward direction when the implant is expanded. Expansion is caused by turning screw 42.

The disk implants of the present invention are expandable in the middle portion, i.e., the portion intermediate the ends, so as to contact substantially the entire anterior-posterior length of the disk space against the vertebral bodies. If a complete intervertebral fusion is being performed, the plug of the present invention is used in conjunction with intervertebral cancellous bone packing. Because of the support provided by the plug, in the initial stages until the fusion is established, the cancellous bone pieces have a better chance of fusion due to the presence of the implant, and the bone pieces and the disk implant have a better chance of staying in the intervertebral disk space. Alternatively, the intervertebral disk plug is used to maintain the disk height and can be used in conjunction with intertransverse posterior lateral fusion. In short, this plug, which can be expanded in the middle, acts as a physiological support for the rest of the patient's life or until a bone fusion is established.

The disk implant of the present invention may have additional indications, e.g. short segment scoliosis, where the curvature of the spine can be corrected by distracting the vertebral bodies on the inside of the curvature. By expanding the plugs inside the disk space, the vertebral bodies are distracted, thereby helping straighten the spinal column.

If no bone graft is being planned, it is recommended that the diskectomy be made minimally through one side exposure so that when the disk plug is inserted and expanded, it will take the empty room in the space. Because there is no further movement at this disk space, the chance of recurrent disk herniation is minimized. Also, the likelihood of recurrent disk herniation due to the opening and closing effect of the disk space on the side of the diskectomy is reduced because the disk plug closes this mouth, e.g., the mouth cannot be opened and closed. Consequently, by using this process, in addition to the advantages of a one sided, simple diskectomy, the risk of recurrent disk herniation can be reduced.

By reference to the figures, it can be seen that there are multiple presently preferred embodiments of disk plugs; one is substantially rectangular and the other substantially cylindrical, and these shapes can result from the use of different structure in the implant. Both have the common feature of being expandable in the middle without changing the diameter of the dimensions of the two ends. The surgery is performed as in simple diskectomy, and the disk is exposed through a small laminotomy. The disk material is removed and any nerve root compression is corrected. The posterior longitudinal ligament and disk cartilage are removed until the vertebral surfaces are exposed above and below the disk space. The shape of the disk space determines whether the disk plug used is cylindrical or rectangular. The disk plug is then inserted and hammered into place so that the anterior end of the disk plug almost touches the anterior longitudinal ligament. Subsequently, using a Phillips screwdriver, the posterior screw end is turned. This implant method also gives good distraction to the vertebral bodies. In the case of simple disk problems, no further treatment may be required.

When used alone without bone grafts, the disk implants of the present invention reduce the possibility of recurrent disk herniations. This reduction, as set out above, is accomplished by a decrease in the mobility of the disk and the decrease in the disk mouth space.

In the preferred embodiment, however, the implants are used in interbody fusion, in which cancellous bone chips are made into very fine particles and pumped into the disk space medial to the disk plug and packed into the space. So as to minimize the volume of bone chips required for this purpose, the volume of the space is minimized by maximizing the thickness of the subunits 34 and 36, or the coiled members 32 (hence the sheath 44 formed in subunits 34 and 36 so that the implant 31 is of minimal vertical dimension). The posterior longitudinal ligament is intact to the opposite side and to the center of the disk space. These cancellous bone chips are held tightly in place. Since the mouth of the disk space is closed with the disk plug, the risk of the cancellous bone chips coming out is minimized. Also, the disk plug prevents the opening and closing of the disk space, thus preventing the bone chips coming out. If necessary, a small amount of a physiologically compatible adhesive of a type known in the art is applied over the cancellous bone chips just medial to the disk plug to close off the remaining portion of the opening of the disk space. The patient should be able to ambulate soon after the surgery because of the stability given by the disk plug. Before narrowing of the disk space occurs, the cancellous bone chips will have started the fusion process.

If on the other hand, a posterior lateral intertransverse fusion is desired, this procedure is also done in conjunction with the middle expandable disk plug. The disk plug is applied as explained above and then the surgeon does the posterior lateral fusion. Since the disk plug provides stability to the spine until the posterior lateral fusion is solid, the patient can ambulate soon after the surgery. This procedure also prevents the disk space narrowing, which is a common problem with posterior lateral fusion.

The disk plugs of the present invention are made of any suitable material including a material like modified carbon so that they will be magnetic resonance imaging (MRI) compatible. This imaging method is a simple and safe procedure with a wide range of applications in the management of low back pain. The same plug in smaller dimensions is used in thoracic and cervical levels where indicated. In the neck, the implant is used following anterior cervical diskectomy without the risk of the plug migrating anteriorly or posteriorly.

There is provided in the preferred embodiments an artificial intervertebral disk implant having a cylindrical body comprised of cylindrical coils capable of expansion and an intervertebral disk implant having either a rectangular or generally cylindrical body comprised of rectangular blocks capable of expansion in the middle. Both the cylindrical and rectangular implants are disk plugs being expandable in the middle portion so as to provide contact with substantially the entire anterior posterior length of the disk space against the vertebral bodies.

The present invention recognizes and addresses the previously mentioned long felt needs and provides a satisfactory meeting of those needs in its various possible embodiments. To one of skilled in this art who has the benefits of this invention's teachings and disclosures, other and further objects and advantages will be clear as well as others inherent from the preceding description of the presently preferred embodiments thereof.

What is claimed is:

1. An implant for disposition in the space between two adjacent vertebrae after removal of a portion of the intervertebral disk therefrom comprising:

an elongate, threaded rod;

a first end cap mounted to said rod;

a second end cap threadedly engaging said rod for moving along said rod relative to said first end cap when said rod is rotated along the threads on said rod; and a plurality of hinged subunits mounted between said first and second end caps and hingedly connected thereto, said hinged subunits comprising hinges which are movable from a first position surrounding and in close proximity to said rod so as to minimize the vertical dimension of the implant to facilitate insertion into the opening of the disk space to a second position with maximal vertical dimension by radially outward expansion of the hinges of said hinged subunits upon rotation of said rod after insertion into the disk space from which a portion of the disk has been removed to conform the shape of the implant to the shape of the anatomical region of the space from which the disk has been removed.

2. The implant of claim 1 additionally comprising a lock nut for engaging said rod to prevent rotation of said rod after expansion of the hinges of said subunits to said second position.

3. The implant of claim 1 wherein said second end cap receives said rod in a threaded hole, said rod being inlaid in said second end cap.

4. The implant of claim 1 additionally comprising means for preventing rotation of said rod after expansion of the hinges of said hinged subunits from said first position to said second position.

5. The implant of claim 4 wherein said rotation preventing means is inlaid in said second end cap.

6. The implant of claim 4 wherein said rotation preventing means comprises a screw threadably engaging the threads in said second end cap.

7. The implant of claim 1 wherein said hinged subunits are angled.

8. The implant of claim 1 wherein said hinged subunits are provided with bearing surfaces which cause the hinges of said hinged subunits to tend to move radially outwardly from said first position to said second position upon rotation of said rod.

9. The implant of claim 1 wherein said hinged subunits are provided with beveled sides to minimize the vertical dimension of the implant when said hinged subunits are in said first position.

* * * * *